(12) United States Patent
Calder et al.

(10) Patent No.: US 8,729,124 B2
(45) Date of Patent: May 20, 2014

(54) USE OF EPA AND DHA IN SECONDARY PREVENTION

(75) Inventors: Philip Calder, Southampton (GB); Robert Grimble, Southampton (GB); Patrick Gallagher, Bath (GB); Cliff Shearman, Romsey (GB)

(73) Assignee: Pronova Biopharma Norge AS, Baerum (NO)

( * ) Notice: Subject to any disclaimer, the term of this patent is extended or adjusted under 35 U.S.C. 154(b) by 963 days.

(21) Appl. No.: 10/979,751

(22) Filed: Nov. 2, 2004

(65) Prior Publication Data

US 2005/0171200 A1    Aug. 4, 2005

Related U.S. Application Data

(63) Continuation of application No. PCT/GB03/01945, filed on May 2, 2003.

(30) Foreign Application Priority Data

Mar. 5, 2002  (GB) .................................. 0210212.7
Feb. 4, 2003  (GB) .................................. 0307625.4

(51) Int. Cl.
 *A61K 31/202*  (2006.01)
 *A61K 31/232*  (2006.01)

(52) U.S. Cl.
 CPC ............. *A61K 31/202* (2013.01); *A61K 31/232* (2013.01); *A61K 2300/00* (2013.01); *Y10S 514/824* (2013.01)
 USPC ............................. 514/549; 514/560; 514/824

(58) Field of Classification Search
 None
 See application file for complete search history.

(56) References Cited

U.S. PATENT DOCUMENTS

| | | | | |
|---|---|---|---|---|
| 5,656,667 A | * | 8/1997 | Breivik et al. | ................ 514/560 |
| 5,731,346 A | * | 3/1998 | Egberg et al. | ................ 514/549 |
| 5,977,174 A | | 11/1999 | Bradley et al. | |
| 6,153,653 A | | 11/2000 | Shashoua | |
| 2003/0215430 A1 | * | 11/2003 | Petrus | .......................... 424/94.1 |

FOREIGN PATENT DOCUMENTS

| | | |
|---|---|---|
| EP | 1 163 905 | 12/2001 |
| EP | 1 419 780 | 5/2004 |
| GB | 2 216 421 | 10/1989 |
| GB | 2 216 421 A | 10/1989 |
| GB | 2 218 904 | 11/1989 |
| JP | 5-271685 | 10/1993 |
| JP | 8-175988 | 7/1996 |
| JP | 9-508619 | 9/1997 |
| JP | 10-147522 | 6/1998 |
| JP | 11-80083 | 3/1999 |
| JP | 2001-131088 | 5/2001 |
| WO | WO 00/32184 | 6/2000 |
| WO | WO00/32184 A1 | 6/2000 |
| WO | WO 00/44360 A2 | 8/2000 |
| WO | WO 00/44361 | 8/2000 |
| WO | WO 00/48592 | 8/2000 |
| WO | WO 01/03696 A1 | 1/2001 |
| WO | WO 01/76568 A2 | 10/2001 |
| WO | WO 01/84961 | 11/2001 |
| WO | WO 01 84961 A | 11/2001 |
| WO | WO 01/84961 A2 | 11/2001 |
| WO | WO 01/85201 | 11/2001 |

OTHER PUBLICATIONS

Delcker et al. Influence of vascular risk factors for atherosclerotic carotid artery plaque progression. Stroke. 1995; 26(11): 2016-2022; electronic copy, pp. 1-17.*
(Su et al. Hypertension status is the major determinant of carotid atherosclerosis. A community-based study in Taiwan. Stroke. 2001;32:2265-2271.*
Lonn et al. Effects of ramipril and vitamin E on atherosclerosis. The study to evaluate carotid ultrasound changes in patients treated with ramipril and vitamin E (Secure) (Circulation. 2001;103:919-925.*
Treatment for Stroke. The University of Chicago Medical Center, 2007, electronic copy, pp. 1-3.*
Véricel et al., "The influence of low intake of n-3 fatty acids on platelets in elderly people," Atherosclerosis 147, 187-192 (1999).
Abbate et al., "n-3 PUFA supplementation, monocyte PCA expression and interleukin-6 production," Prostaglandins, Leukotrienes and Essential Fatty Acids 54(6), 439-444 (1996).
Hamazaki et al., "Effects of fish oil rich in eicosapentaenoic acid on serum lipid in hyperlipidemic hemodialysis patients," Kidney International, vol. 26, pp. 81-84 (1984).
Drugs in Japan, Japan Pharmaceutical Information Center, Oct. 25, 1999, 2000-version, pp. 201-202.
English translation of portions of Drugs in Japan, Japan Pharmaceutical Information Center, Oct. 25, 1999, 2000-version, pp. 201-202.
English Abstract for WO 00/32184 on cover page of International Application Publication WO 00/32184.
European Pharmacopoeia, pp. 3571-3572.
Fyfe, D. J. and Abbey, M. "Effects of n-3 fatty acids on growth and survival of J774 macrophages" *Prostaglandins, Leukotrienes and Essential Fatty Acids* (2000) 62(3):201-207.
Garry, J. M. et al. "Effect of dietary n-3 and n-6 PUFA intake on LDL oxidizability and fatty acid composition in patients with advanced atherosclerosis" *Proceedings of the Nutrition Society* (2000) 60:32A.
Iezzi, A. et al. "N-3 polyunsaturated fatty acids stabilize atherosclerotic plaques in humans by inhibiting pge2-dependent matrix metalloproteinase activity" *Eur. Heart J.* (2006) 27(Abstract Suppl):5.
Kinsella, J. E. et al. "Dietary n-3 polyunsaturated fatty acids and amelioration of cardiovascular disease: possible mechanisms" *Am. J. Clin. Nutr.* (1990) 52:1-28.

(Continued)

Primary Examiner — Daniel Sullivan
Assistant Examiner — Barbara Frazier
(74) Attorney, Agent, or Firm — Finnegan, Henderson, Farabow, Garrett & Dunner, L.L.P.

(57) ABSTRACT

The invention is directed to a method for preventing cerebral damage in patients having symptoms of atherosclerosis of arteries supplying the brain by administering to the patient a therapeutically effective amount of a composition comprising eicosapentaenoic acid (EPA), docosahexaenoic acid (DHA) or a combination thereof.

10 Claims, No Drawings

(56) References Cited

OTHER PUBLICATIONS

Nanzando's Medical Dictionary, Nanzando Co., Ltd., 18th Ed., pp. 106-107.

English translation of portions of Nanzando's Medical Dictionary, Nanzando Co., Ltd., 18th Ed., pp. 106-107.

Nanzando's Medical Dictionary, Nanzando Co., Ltd., 18th Ed., pp. 932 and 1493-1494.

English translation of portions of Nanzando's Medical Dictionary, Nanzando Co., Ltd., 18th Ed., pp. 932 and 1493-1494.

Rapp, J. H. et al. "Dietary Eicosapentaenoic Acid and Docosahexaenoic Acid From Fish Oil: Their Incorporation Into Advanced Human Atherosclerotic Plaques" *Arteriosclerosis and Thrombosis* (1991) 11:903-911.

Goodnight et al., Polyunsaturated fatty acids, hyperlipidemia, and thrombosis, 2 Arterioscience 87-113 (1982).

Giraldo, Elias A., MD, Transient Ischemic Attacks, Merck Manual Home Edition, Nov. 2007.

Thies et al., Association of n-3 polyunsaturated fatty acids with stability of atherosclerotic plaques: a randomized controlled trial, 361Lancet 477-85 (2003).

Green et al., A double-blind, placebo-controlled trial of fish oil concentrate (MaxEpa) in stroke patients, 16 Stroke 706-709 (1985).

Willumsen et al., On the effect of 2-deuterium- and 2-methyl-eicosapetaenoic acid derivatives on triglycerides, peroxisomal β-oxidation and platelet aggregation in rats, 1369 Biochimica et Biophysica Acta 193-203 (1998).

Hata, Y. et al., *Biomedicine and Therapeutics* (1991) 25(1):124-128.

English translation of portions of *Biomedicine and therapeutics* (1991) 25(1):124-128.

Cawood, L. et al. "Long chain omega-3 fatty acids enter advanced atherosclerotic plaques and are associated with decreased inflammation and decreased inflammatory gene expression" *XIV International Symposium on Atherosclerosis*, Rome, Italy, Jun. 18-22, 2006.

Dialog English abstract of JP 10-147522. (1998).

Dialog English abstract of JP 11-80083. (1999).

Dialog English abstract of JP 2001-131088. (2001).

Dialog English abstract of JP 5-271685. (1993).

Dialog English abstract of JP 8-175988 and Dialog English translation of JP 9-508619. (1996).

* cited by examiner

USE OF EPA AND DHA IN SECONDARY PREVENTION

CROSS REFERENCE TO RELATED APPLICATIONS

This application is a continuation of International Application No. PCT/GB03/01945, filed on May 2, 2003, and published in English on Nov. 13, 2003 as WO 03/092673 A1, which claims priority from Great Britain patent applications GB 0210212.7 filed on May 3, 2002 and GB 0307625.4 filed on Apr. 2, 2003, the entire disclosures of which are incorporated herein by reference.

The present invention relates to the use of the n-3 PUPA eicosapentaenoic acid (EPA) and/or docosahexaenoic acid (DHA) in the prevention of secondary neurological events, particularly strokes, in patients with symptoms of atherosclerosis of arteries supplying the brain.

There is a substantial epidemiological evidence that consumption of fish or of long-chain n-3 polyunsaturated fatty acids (PUFA), especially EPA and DHA, found in oily fish and fish oils, protects against cardiovascular disease in Western populations. Long chain n-3 PUFA lower fasting plasma triacylglycerol (TAG) concentrations and reduce the postprandial lipaemic response. Dietary fish oil has been demonstrated to decrease atherosclerosis in animal models, which might be due to lipid lowering, decreased growth factor production, decreased inflammation, or a combination of these effects. Secondary prevention studies, providing long chain n-3 PUPA to patients who had already suffered a myocardial infarction (MI), demonstrate significant benefit, as described and claimed in: EP-B-1 152 755. N-3 PUFA are especially potent in reducing sudden death, (EP-B-1 152 755), an effect that occurs in the absence of significant lipid lowering. It has been surmised that this effect might be due to anti-thrombotic and anti-arrhythmic actions of n-3 PUFA. In contrast, we have thought it possible that n-3 PUPA might contribute to the stabilisation of atherosclerotic plaques through their anti-inflammatory actions. Conversely, there are indications that n-6 PUFA linoleic acid, which is found in vegetable oil such as sunflower oil, can promote inflammation, in which case an increased intake of linoleic acid might contribute to plaque instability.

To our knowledge there are no studies reporting effects of n-6 or n-3 PUPA on plaque stability. Rapp et al (Arterioscler. Thromb. 1991, II, 903-911) carried out a study in which patients destined to undergo endarterectomy consumed very high doses of fish oil (48-64 g/day) for a period prior to surgery and they found that the levels of the n-3 PUFA, eicosapentaenoic acid (EPA; 20:5n-3) and docosahexaenoic acid (DHA; 22:6n-3) in the plaques removed at surgery were significantly higher than in plaques removed from control patients. However, Rapp et al provided no structural details of the plaques.

We have now found, in accordance with the present invention, that the administration of relatively modest doses of fish oil to patients with symptoms of atherosclerosis of arteries supplying the brain not only results in incorporation of EPA and DHA into low density lipoprotein (LDL) and atherosclerotic plaque lipids but, significantly, also leads to improved atherosclerotic plaque stability.

More particularly, we have discovered that such patients who are given fish oil orally tend to have more plaques with a well-formed fibrous cap, rather than a thin inflamed cap, and further the plaques are less heavily infiltrated with macrophages. As is well known the characteristics of an atherosclerotic plaque that make it vulnerable to rapture include a thin fibrous cap and increased numbers of inflammatory cells such as macrophages The presence of macrophages in carotid plaques is also known to be associated with an increased incidence of neurological events i.e. strokes and transient ischaemic attacks. Consequently, the oral administration of fish oil provides an effective, and safe, method for helping to prevent neurological events, particularly strokes, in patients with symptoms of atherosclerosis of arteries supplying the brain.

Thus, the present invention is directed to the use of EPA and/or DHA in the preparation of an oral medicament for preventing cerebral damage in patients having symptoms of atherosclerosis of arteries supplying the brain.

In a preferred embodiment of the invention the oral medicament is for preventing a stroke in a patient with a symptom of cerebrovascular accident, amaurosis fugax and/or transient ischaemic attack.

We will now describe in detail the experimental study which has led to the present invention.

Patients and Methods

Study Design

Patients destined to undergo carotid endarterectomy ie exhibiting symptoms of advanced atherosclerosis of arteries supplying the brain, and who agreed to participate were randomised, in a double-blind manner, to receive one of three types of oil provided in capsules. The control oil was an 80:20 blend of palm and soybean oils; the fatty acid composition of this blend closely matches that of the average adult UK diet. The other oils were sunflower oil and an EPA/DHA-containing fish oil. The fatty acid composition of the oils is shown in Table 1. Each capsule contained 1 g of oil and 1 mg α-tocopherol. Patients consumed 6 capsules/day until surgery; patients were recommended to consume two capsules with a meal three times each day. Thus, the amount of long chain n-3 PUFA provided was 1.4 g/day. The amount of linoleic acid provided was 3.6 g/day, which represented a 40% increase in intake of this fatty acid.

TABLE 1

Fatty acid composition of the capsules used in study

| Fatty acid | Fatty acid (g/100 g total fatty acids) | | |
|---|---|---|---|
| | Control | Sunflower oil | Fish oil |
| Lauric (12:0) | 0.9 | — | — |
| Myristic (14:0) | 2.1 | 1.5 | 6.2 |
| Palmitic (16:0) | 34.9 | 8.6 | 20.4 |
| Palmitoleic (16:1n – 7) | 2.0 | 1.0 | 12.3 |
| Stearic (18:0) | 3.7 | 3.5 | 5.7 |
| Oleic (18:1n – 9) | 33.8 | 18.6 | 10.1 |
| Linoleic (18:2n – 6) | 18.9 | 62.8 | 2.3 |
| α-Linolenic (18:3n – 3) | 1.8 | 1.4 | 4.6 |
| Arachidonic (20:4n – 6) | — | 1.2 | 1.1 |
| EPA (20:5n – 3) | — | — | 14.3 |
| Docosapentaenoic (22:5n – 3) | — | — | 1.5 |
| DHA (22:6n – 3) | | | 8.3 |

Sample size was calculated based on the fatty acid composition of plaque phospholipids (PL) described by Rapp et al., (Arteriscler. Thromb. 1991 11, 903-11) taking into account the 10- to 15-fold lower dose of EPA+DHA employed in the present study. On this basis it was calculated that a sample size of 50 would be required to detect a 1-fold increase in EPA in plaque PL at $P<0.05$. To allow for a drop-out rate of 20%, 188 patients were recruited into the study.

At entry to the study a fasting venous blood sample was taken into EDTA. Patients then commenced consumption of capsules as described above, and completed a 7-day weighed food diary. Patients continued with medications throughout the study period and were advised not to change their diet. Compliance was promoted by regular contact with patients and was assessed by counting returned capsules and by measuring the fatty acid composition of LDL lipid fractions. Patients who reported an inability to comply (n=5) were withdrawn from the study. Returned capsule counts suggested compliance >85% in each treatment group. Furthermore, the proportion of EPA in each plasma LDL lipid fraction increased by more than 0.5 g/100 g total fatty acids in >90% of patients in the fish oil group. These observations indicate that compliance was at least 85 to 90% in each treatment group.

Surgical removal of carotid plaques was performed generally between 7 and 190 days after patients' entry into the study. Patients who went to surgery within 7 days were excluded from the study. On the morning prior to surgery a second fasting venous blood sample was taken. At surgery the carotid plaque was collected and rinsed. It was then cut into cross-sections 2 mm in width staring at the common carotid artery. Sections for biochemical analysis were frozen in liquid nitrogen. Sections for histology were fixed in formaldehyde and then embedded in pain wax. Sections for immunohistochemistry were frozen in optimal cutting temperature embedding medium (Agar Scientific, Stansted, UK), and stored at −70° C.

Analysis of Habitual Nutrient Intakes

Food diaries were analysed for habitual nutrient intakes using a modification of FOODBASE (Institute of Brain Chemistry, London, UK), which has been validated for determination of fatty acid intakes.

Plasma Lipids and Lipoproteins

Plasma total cholesterol and triacylglycerol (TAG) concentrations were determined using commercially available colorimetric assays (Sigma Chemical Co., Poole, UK). Low density lipoproteins (LDL) were prepared from plasma on a two-step density gradient formed by layering 1.7 mL of plasma (adjusted to a density of 1.24 g/mL by addition of solid potassium bromide) under 3.3 mL of phosphate-buffered saline and centrifuging in sealed tubes at a speed of 100,000 rpm for 2 h at 15° C. in a Beckman TLA-100.4 rotor in a Beckman Optima ultracentifuge. Purified LDL were frozen at −70° C. for fatty acid composition analysis.

Fatty Acid Composition Analyses

The fatty acid compositions of the PL, cholesteryl ester (CE) and TAG fractions of LDL and of the frozen section closest to the bifurcation of the carotid plaques were determined. Total lipid was extracted, lipid fractions separated by thin layer chromatography and the fatty acid composition of each fraction determined by gas chromatography as described by Thies et al. (Am. J. Clin. Nutr. 2001, 73, 539-48).

Morphology of Carotid Plaques

Paraffin embedded sections were stained with haematoxylin and eosin. The section closest to the bifurcation was classified using both the guidelines published by the American Heart Association (Stary et al., Circulation, 1995, A, 1355-74) and also using a modification of this system proposed by Virmani et al. (Arterioscler. Thromb. Vasc. Biol. 2000 20, 1262-75). Sections were examined by a cardiovascular pathologist (PJG) in random order and without access to any patient information. The American Heart Association (AHA) classification involves six grades, or types, as follows: Type I (initial lesion); Type II (early lesion or fatty-streak); Type III (intermediate lesion or pre-atheroma); Type IV (atheroma or atheromatous plaque); Type V (fibroatheroma or fibrotic lesion); Type VI (lesion with surface defect and/or haemorrhage and/or thrombotic deposit). The modification of this classification proposed by Virmani et al. involves a series of descriptive grades of increasing severity as follows: pathological intimal thickening (smooth muscle cells in the matrix with areas of extracellular lipid accumulation but no necrosis or thrombus); fibrous cap atheroma (a well formed necrotic core with an overlying fibrous cap; no thrombus); thin fibrous cap atheroma (a thin fibrous cap infiltrated by macrophages and lymphocytes with rare smooth muscle cells and an underlying necrotic core; no thrombus); erosion (luminal thrombosis); plaque rupture (fibroatheroma with disruption; luminal thrombus communicating with necrotic core); calcified nodule and fibrocalcific plaque (eruptive calcification).

Immunohistochemistry of Carotid Plaques

The plaque section second from the bifurcation was used for immunohistochemistry. Sections were stained for the presence of macrophages (distinguished by the presence of CD68 on their surface) and T lymphocytes (distinguished by the presence of CD3 on their surface) and for two adhesion molecules, vascular cell adhesion molecule-1 (VCAM-1) and intercellular adhesion molecule-1 (ICAM-1), involved in movement of immune cells into the plaque. Cryostat sections of frozen plaque were mounted on organosilan-coated microscope slides. Endogenous peroxidase activity was blocked and then the sections were successively incubated with optimal dilutions of the different anti-human antibodies, biotinylated goat anti-mouse (swine anti-goat for staining of VCAM-1) immunologobulin G (DAKO, Ely, UK), and streptavidin-horseradish peroxidase (DAKO, Ely, UK). Finally, peroxidase activity was visualised using hyrogen peroxide as substrate and 3-amino-9-ethyl carbazole (Sigma Chemical Co., Poole, UK) as chromogen. Stained sections were fixed using formalin, counterstained with Harris hematoxylin, and viewed using a microscope under 10× power of magnification. Primary antibodies used were mouse anti-human CD3 (Leu 4; Becton Dickinson, Oxford, UK), mouse anti-human CD68 (KP1; DAKO, Ely, UK); mouse anti-human ICAM-1 (R & D Systems, Oxford, UK), and goat anti-human VCAM-1 (R & D Systems, Oxford, UK). Staining was ranked 0 (no staining), 1 (moderate staining) or 2 (heavy staining).

Statistical Analysis

Data are shown only for patients who completed the study (n=57 in the control group; n=52 in the sunflower oil group; n=53 in the fish oil group). Age, body mass index (BMI), blood lipid concentrations at study entry, clinical history, medication use and habitual nutrient intakes among the different treatment groups were compared using one-factor ANOVA. The effects of treatment on blood lipid concentrations and on the fatty acid compositions of LDL lipid fractions were determined as change from baseline value. Changes from baseline among the different treatment groups were compared by one-factor ANCOVA using baseline value and duration of treatment as co-variates; where there was a significant effect of treatment Student's t-test was used to identify differences between groups. In some cases post-treatment values were compared with baseline values within the same treatment group by the paired Student's t-test and post-treatment values were compared among treatment groups by one-factor ANOVA with post-hoc Student's t-test. The fatty acid compositions of carotid plaque lipid fractions among the different treatment groups were compared using one-factor ANCOVA, using duration of oil treatment as covariate; where there was a significant effect of treatment Student's t-test was used to identify differences between groups. The distributions of staining intensity (immunohistochemistry) and of plaque morphology were compared among treatment groups using the Chi-squared test. The mean rank of each distribution in each treatment group was determined and these were compared using the Jonckheere-Terpstra test. Correlations were determined as Spearman's correlation coefficients ($\rho$). All analyses were performed using SPSS version 11 (SPSS, Chicago, Ill., USA) and in all cases a value for P<0.05 was taken to indicate a statistically significant difference.

Results

Patient Characteristics

Eighteen patients withdrew from the study, 13 for clinical reasons and 5 because they could not comply with the study protocol. A further 8 patients were excluded from the study because they went to surgery within 7 days of entry to the study.

The characteristics of the patients who completed the study are shown in Table 2. There were no significant differences among the treatment groups at study entry with respect to gender mix, age, BMI, fasting plasma TAG and cholesterol concentrations, intake of energy and of individual macro- and micronutrients including individual fatty acids, number of smokers/ex-smokers, degree of stenosis of the affected carotid artery, clinical history and use of medications (all P>0.1438 at least; one-factor ANOVA) (Table 2). Each group received the supplemented oils for similar durations (Table 2). Patients in the sunflower oil group received an extra 3.6 g linoleic acid/day, increasing daily consumption of this fatty acid by about 40%. Patients in the fish oil group received an extra 1.4 g long chain n-3 PUFA/day, increasing EPA intake approximately 10-fold and DHA intake approximately 4-fold.

TABLE 2

Patient characteristics at study entry

|  | Control | Sunflower oil | Fish oil |
|---|---|---|---|
| Male (n) | 36 | 32 | 33 |
| Female (n) | 21 | 20 | 20 |
| Age (years) | 70 ± 8 | 69 ± 9 | 69 ± 9 |
|  | (38-85) | (44-83) | (52-84) |
| BMI (kg/m2) | 26.4 ± 4.1 | 25.9 ± 3.5 | 25.9 ± 4.2 |
|  | (19.1-37.1) | (20.1-34.1) | (17.1-42.4) |
| Plasma TAG (mmol/L) | 1.7 ± 0.8 | 1.8 ± 1.1 | 1.7 ± 1.3 |
| Plasma cholesterol (mmol/L) | 4.8 ± 1.2 | 4.7 ± 0.9 | 4.8 ± 1.0 |
| Energy intake (kcal/day)† | 1833 ± 377 | 1911 ± 496 | 2004 ± 437 |
| Habitual fatty acid intakes (g/day)† |  |  |  |
| Linoleic acid | 8.5 ± 3.2 | 9.2 ± 4.9 | 8.1 ± 4.1 |
| Arachidonic acid | 0.06 ± 0.06 | 0.05 ± 0.06 | 0.05 ± 0.06 |
| α-Linolenic acid | 0.91 ± 0.51 | 0.82 ± 0.31 | 0.98 ± 0.47 |
| EPA | 0.11 ± 0.12 | 0.11 ± 0.06 | 0.08 ± 0.06 |
| DHA | 0.15 ± 0.19 | 0.13 ± 0.13 | 0.10 ± 0.12 |
| Current smokers (n) | 7 | 9 | 5 |
| Ex-Smokers (n)* | 42 | 39 | 40 |
| Clinical history (n) |  |  |  |
| Symptoms in the 6 months prior to study entry | 39 | 31 | 35 |
| Cerebrovascular accident¶ | 6 | 9 | 11 |
| Amaurosis Fugax‡ | 14 | 13 | 20 |
| Transient ischaemic attack | 22 | 20 | 14 |
| Symptoms more than 6 months prior to study entry | 22 | 21 | 22 |
| Cerebrovascular accident¶ | 8 | 9 | 11 |
| Amaurosis Fugax | 7 | 7 | 6 |
| Transient ischaemic attack | 12 | 14 | 10 |
| Angina | 21 | 17 | 18 |
| Myocardial infarction | 11 | 9 | 11 |
| Aortic aneurysim | 4 | 3 | 1 |
| Previous coronary artery bypass graft | 12 | 4 | 4 |
| Hypertension | 44 | 33 | 35 |
| Diabetes | 10 | 10 | 11 |
| Stenosis (%) | 95 (80, 95) | 90 (80, 95) | 90 (80, 95) |
| Medication use (n) |  |  |  |
| Aspirin | 57 | 52 | 53 |
| β-Blockers | 13 | 14 | 12 |
| ACE inhibitors | 16 | 9 | 9 |
| Nitrates | 9 | 10 | 11 |
| Calcium channel blockers | 23 | 15 | 20 |
| Fibrates | 1 | 1 | 3 |
| Statins | 19 | 18 | 17 |
| Insulin | 1 | 1 | 5 |
| Oral antidiabetics | 9 | 6 | 6 |
| Duration of oil treatment (days) | 34 (14, 95) | 43 (17, 101) | 46 (15, 100) |

Data for age, BMI, blood lipids and nutrient intakes are mean ± SD (age and BMI ranges are shown in parentheses).
Data for stenosis are median with $25^{th}$ and $75^{th}$ centiles shown in parentheses.
Data for duration of oil treatment are median with $10^{th}$ and $90^{th}$ centiles shown in parentheses.
†data are calculated from 7-day weighed food diaries.
*most ex-smokers had given up smoking more than 3 years before entry into the study.
¶i.e. stroke.
‡temporary partial or complete loss of sight.

Plasma Lipid Concentrations

There was no significant effect of treatment on plasma cholesterol concentration (data not shown). However, there was a significant effect of treatment on plasma TAG concentration (P=0.0184; one-factor ANCOVA). Fish oil resulted in a significant decrease (−0.48±1.06 mmol/L) in plasma TAG concentration, which was not significantly changed in the other groups. Thus, plasma TAG concentration was significantly lower after fish oil treatment (1.2±0.8 mmol/L) compared with at baseline (P=0.0032; paired Student's t-test). Furthermore, plasma TAG concentration in the fish oil group at the end of treatment was significantly lower than that in the other two groups (P=0.0294 vs. control and P=0.0347 vs. sunflower oil; one-factor ANOVA). There was a significant linear correlation between duration of treatment with fish oil and change in plasma TAG concentration (p=−0.44; P=0.0118).

Fatty Acid Composition of LDL Lipid Fractions

There was a significant effect of treatment on the proportions of several fatty acids in LDL PL, CE and TAG. The proportions of EPA and DHA increased in all three LDL lipid fractions after fish oil treatment (Table 3). These proportions were significantly different from baseline (P<0.0001 for EPA in each fraction, P=0.0031 for DHA in CB, P<0.0001 for DHA in PL and TAG; paired Student's t-test) and from those in the other two groups after treatment (P<0.0003 at least; one-factor ANOVA). Increases in the proportions of the long chain n-3 PUFA in LDL PL in the fish oil group were accompanied by significant decreases in the proportions of linoleic, di-homo-γ-linolenic (20:3n-6) and arachidonic (20:4n-6) acids. Increases in the proportions of the long chain n-3 PUFA in LDL CE and TAG in the fish oil group were accompanied by significant decreases in the proportions of linoleic and oleic (18:1n-9) acids, respectively. Sunflower oil treatment resulted in an increased proportion of linoleic acid in LDL CE, largely at the expense of oleic acid. These observations are summarized in Table 3.

TABLE 3

Effects of dietary oil treatment on the fatty acid composition of LDL lipid fractions

| | | Fatty acid (g/100 g total fatty acids) | | | | | | One-factor ANCOVA effect of treatment |
|---|---|---|---|---|---|---|---|---|
| | | Control | | Sunflower oil | | Fish oil | | |
| | | Baseline | Change | Baseline | Change | Baseline | Change | P |
| PL | 18:1n-9 | 11.4 ± 1.9 | -0.1 ± 1.2$^a$ | 11.6 ± 1.8 | -0.7 ± 1.2 | 11.7 ± 2.2 | -1.1 ± 1.4$^b$ | <0.0001 |
| | 18:2n-6 | 19.5 ± 3.2 | 0.1 ± 1.4$^a$ | 19.9 ± 2.5 | 0.3 ± 1.6$^a$ | 20.4 ± 2.8 | -2.7 ± 1.7$^b$ | <0.0001 |
| | 20:3n-6 | 3.4 ± 0.8 | -0.1 ± 0.6$^a$ | 3.2 ± 0.7 | 0.1 ± 0.6$^a$ | 3.4 ± 0.6 | -1.0 ± 0.6$^b$ | <0.0001 |
| | 20:4n-6 | 8.8 ± 1.8 | 0.1 ± 1.3$^a$ | 8.3 ± 1.8 | 0.3 ± 1.3 | 8.7 ± 1.6 | -1.0 ± 1.4$^b$ | <0.0001 |
| | 20:5n-3 | 1.0 ± 0.4 | 0.0 ± 0.4$^a$ | 1.3 ± 0.6 | -0.1 ± 0.4$^a$ | 1.3 ± 0.9 | 2.4 ± 1.3$^b$ | <0.0001 |
| | 22:5n-3 | 1.8 ± 0.9 | -0.1 ± 0.9$^a$ | 2.0 ± 1.0 | -0.3 ± 0.9$^a$ | 1.9 ± 0.9 | 0.2 ± 0.8$^b$ | <0.0001 |
| | 22:6n-3 | 3.3 ± 1.1 | 0.3 ± 1.1$^a$ | 3.7 ± 1.4 | 0.1 ± 0.9$^a$ | 3.4 ± 1.4 | 2.5 ± 1.7$^b$ | <0.0001 |
| CE | 18:1n-9 | 19.4 ± 2.2 | -0.7 ± 1.8$^a$ | 19.4 ± 2.8 | -1.7 ± 2.2$^b$ | 19.2 ± 2.6 | -0.2 ± 2.1$^a$ | 0.0013 |
| | 18:2n-6 | 49.2 ± 4.5 | -1.0 ± 3.6 | 48.3 ± 5.4 | 3.0 ± 3.7$^a$ | 49.4 ± 4.6 | -1.9 ± 3.5$^b$ | <0.0001 |
| | 20:4n-6 | 6.1 ± 1.6 | 0.1 ± 0.9$^a$ | 7.0 ± 1.7 | -0.7 ± 1.9 | 6.7 ± 1.6 | -1.0 ± 0.8$^b$ | 0.0022 |
| | 20:5n-3 | 1.1 ± 0.8 | -0.1 ± 1.0$^a$ | 1.3 ± 0.8 | -0.3 ± 0.8$^a$ | 1.2 ± 0.8 | 3.1 ± 1.3$^b$ | <0.0001 |
| | 22:6n-3 | 1.0 ± 0.9 | 0.1 ± 0.8$^a$ | 1.0 ± 0.7 | -0.1 ± 0.8$^a$ | 1.0 ± 0.6 | 0.9 ± 1.3$^b$ | <0.0001 |
| TAG | 18:1n-9 | 41.4 ± 3.5 | -1.1 ± 2.6$^a$ | 41.6 ± 3.9 | -2.1 ± 3.3 | 43.4 ± 3.4 | -4.2 ± 2.6$^b$ | 0.0012 |
| | 18:2n-6 | 15.0 ± 3.3 | 1.9 ± 3.2 | 14.7 ± 3.1 | 1.1 ± 3.5 | 15.4 ± 3.9 | 0.2 ± 1.7 | 0.4613 |
| | 20:4n-6 | 1.6 ± 0.7 | 0.2 ± 0.4 | 1.6 ± 0.7 | 0.2 ± 0.5 | 1.7 ± 0.6 | 0.1 ± 0.6 | 0.6385 |
| | 20:5n-3 | 0.5 ± 0.4 | 0.0 ± 0.2$^a$ | 0.5 ± 0.3 | 0.2 ± 0.7$^a$ | 0.5 ± 0.2 | 1.4 ± 1.0$^b$ | 0.0064 |
| | 22:5n-3 | 0.4 ± 0.3 | 0.1 ± 0.3$^a$ | 0.5 ± 0.3 | 0.1 ± 0.5$^a$ | 0.5 ± 0.3 | 1.2 ± 1.3$^b$ | 0.0076 |
| | 22:6n-3 | 0.9 ± 0.6 | 0.2 ± 0.4$^a$ | 1.0 ± 0.6 | 0.3 ± 0.5$^a$ | 0.9 ± 0.6 | 1.5 ± 1.3$^b$ | <0.0001 |

Data are mean ± SD.
Change values across a row indicated by different superscript letters are significantly different from one another (one-factor ANCOVA using baseline value and duration of treatment as co-variates).

Fatty Acid Composition of Carotid Plaques

There was a significant effect of treatment on the proportions of EPA and DHA in each of the plaque lipid fractions and on the proportion of linoleic acid in plaque PL. The proportion of EPA was higher in the PL, CB and TAG of carotid plaques from patients in the fish oil group than in those from patients in the control (P<0.0001, 0.0053 and 0.0007 for PL, CE and TAG, respectively; one-factor ANCOVA) and sunflower oil (P<0.0001, 0.0278 and 0.0024 for PL, CE and TAG, respectively; one-factor ANCOVA) groups. There was a significant positive linear relationship between the proportion of EPA in plaque PL and duration of fish oil treatment (p=0.41, P=0.0051). The proportion of DHA was higher in the CE and TAG of carotid plaques from patients in the fish oil group than in those from patients in the control group (P=0.0042 and 0.0241 for CE and TAG, respectively; one-factor ANCOVA). Furthermore, the proportion of DHA was higher in the PL and CE of carotid plaques from patients in the fish oil group than in those from patients in the sunflower oil group (P=0.0100 and 0.0278 for PL and CE, respectively; one-factor ANCOVA). There was a lower proportion of linoleic acid in PL of plaques from patients in the fish oil group compared with those in the other two groups (P=0.0118 vs. control and P=0.0015 vs. sunflower oil; one-factor ANCOVA). There were no significant differences in the fatty acid compositions of plaque lipid fractions between the control and sunflower oil groups. These observations are summarized in Table 4.

TABLE 4

Fatty acid composition of carotid plaque lipid fractions in different oil treatment groups

| | | Fatty acid (g/100 g total fatty acids) | | | One-factor ANCOVA effect of treatment P |
|---|---|---|---|---|---|
| | | Control | Sunflower oil | Fish oil | |
| PL | 16:0 | 39.1 ± 3.5 | 39.1 ± 4.0 | 39.8 ± 4.5 | 0.4453 |
| | 18:0 | 14.8 ± 1.8 | 14.9 ± 2.1 | 14.9 ± 1.5 | 0.9501 |
| | 18:1n-9 | 14.1 ± 1.6 | 13.7 ± 1.6 | 14.2 ± 2.1 | 0.3152 |
| | 18:2n-6 | 10.9 ± 2.0$^a$ | 11.2 ± 1.9$^a$ | 9.9 ± 1.6$^b$ | 0.0099 |
| | 20:3n-6 | 2.1 ± 0.4 | 2.0 ± 0.5 | 1.9 ± 0.6 | 0.0356 |
| | 20:4n-6 | 10.1 ± 1.8 | 10.1 ± 2.2 | 9.9 ± 2.0 | 0.6412 |
| | 20:5n-3 | 0.6 ± 0.4$^a$ | 0.6 ± 0.5$^a$ | 1.1 ± 0.6$^b$ | <0.0001 |
| | 22:6n-3 | 3.3 ± 1.2 | 2.9 ± 1.0$^a$ | 3.6 ± 1.2$^b$ | 0.0444 |
| CE | 16:0 | 14.5 ± 1.8 | 15.0 ± 1.9 | 14.5 ± 1.7 | 0.1128 |
| | 16:1n-7 | 3.9 ± 1.3 | 4.1 ± 1.3 | 3.8 ± 0.9 | 0.4017 |
| | 18:0 | 1.0 ± 0.6 | 0.7 ± 0.6 | 0.7 ± 0.6 | 0.2171 |
| | 18:1n-9 | 27.3 ± 4.2 | 25.7 ± 3.6 | 26.7 ± 3.2 | 0.1417 |
| | 18:2n-6 | 38.6 ± 6.0 | 40.4 ± 5.4 | 39.5 ± 5.5 | 0.4454 |
| | 20:3n-6 | 2.4 ± 1.1 | 2.1 ± 0.8 | 2.2 ± 1.1 | 0.1268 |
| | 20:4n-6 | 6.6 ± 1.4 | 6.6 ± 1.0 | 6.8 ± 1.1 | 0.8452 |
| | 20:5n-3 | 1.1 ± 0.5$^a$ | 1.1 ± 0.9$^a$ | 1.5 ± 0.5$^b$ | 0.0314 |
| | 22:6n-3 | 1.5 ± 0.6$^a$ | 1.6 ± 0.6$^a$ | 2.0 ± 0.8$^b$ | 0.0084 |
| TAG | 16:0 | 28.9 ± 4.9 | 28.8 ± 3.2 | 27.4 ± 4.5 | 0.3348 |
| | 16:1n-7 | 3.7 ± 1.7 | 3.4 ± 1.0 | 3.8 ± 2.4 | 0.3758 |
| | 18:0 | 5.9 ± 1.9 | 5.8 ± 1.4 | 5.7 ± 1.2 | 0.8954 |
| | 18:1n-9 | 37.8 ± 4.3 | 37.6 ± 2.9 | 38.8 ± 4.3 | 0.2126 |
| | 18:2n-6 | 15.9 ± 4.0 | 16.4 ± 3.3 | 15.1 ± 2.9 | 0.3666 |
| | 20:4n-6 | 2.1 ± 0.9 | 2.2 ± 0.8 | 1.9 ± 0.6 | 0.5016 |
| | 20:5n-3 | 0.2 ± 0.2$^a$ | 0.2 ± 0.2$^a$ | 0.4 ± 0.3$^b$ | 0.0026 |
| | 22:6n-3 | 0.9 ± 0.6$^a$ | 1.0 ± 0.7 | 1.2 ± 0.6$^b$ | 0.0382 |

Data are mean ± SD.
Values across a row indicated by different superscript letters are significantly different from one another (one-factor ANCOVA using duration of treatment as co-variate).

Carotid Plaque Morphologic Classification

The distribution of lesion types determined using the AHA classification was significantly different between patients taking fish oil and those taking the control or sunflower oils (P=0.0234 vs. control and P=0.0107 vs. sunflower oil; Chi-squared test). This appeared to be due to a greater proportion of Type IV lesions ("atheromas") and a lower proportion of Type V lesions ("fibroatheromas and fibrotic lesions") in the fish oil group. The distributions of lesion types from patients treated for shorter or for longer than the median duration in each group were compared. For plaques from patients treated for shorter than the median time, the distribution was not significantly different among the treatment groups. However, the lesion distribution in patients receiving fish oil for longer than the median duration was significantly different from those observed in both the control and sunflower oil groups (P=0.0111 and 0.0432, respectively; Chi-squared test). Across all patients, the EPA and DHA content was highest for Type IV plaques and lowest for Type VI plaques.

The distribution of lesion types determined using the modified AHA classification was significantly different between patients taking fish oil and those taking the control or sunflower oils (P=0.0344 vs. control and P=0.0313 vs. sunflower oil; Chi-squared test). This difference appeared to be due to a greater proportion of lesions with a well-formed fibrous cap and absence of thrombus (fibrous cap atheromas) and a lower proportion of lesions with a thin, inflamed fibrous cap (thin fibrous cap atheromas) in the fish oil group.

There were no significant differences in the distribution of plaque lesion types between the control and sunflower oil groups. These observations are tabulated in Tables 5 and 6.

Lymphocytes and Macrophages in Carotid Plaques

There was no difference in the presence of ICAM-1 or VCAM-1 in plaques from patients in the different treatment groups (data not shown). Likewise, there was no effect of treatment on the presence of T lymphocytes in the plaques. In contrast, plaque sections from patients consuming fish oil were less heavily stained with anti-CD68, a macrophage marker, such that the distribution of staining scores was different for this group compared with the others (P<0.0001 vs. control and P=0.0016 vs. sunflower oil; Chi-squared test) and the mean rank of staining intensity was significantly lower (P=0.0246). Duration of fish oil treatment was significantly negatively correlated with anti-CD68 staining intensity ($\rho$=−0.352; P=0.0301). Plaques from patients taking fish oil for shorter than the median duration of treatment showed a higher intensity of anti-CD68 staining (25% staining intensity 1 and 75% staining intensity 2) than those from patients treated for longer than the median duration (47% staining intensity 1 and 53% staining intensity 2). However, these distributions of staining intensity were not significantly different (P=0.0827, Chi-squared test). The distributions of anti-CD68 staining intensity of plaques from patients treated for shorter or for longer than the median duration in each group were compared. The distributions observed in the fish oil group were significantly different from those observed in both the control (P<0.0001 and 0.0048 for patients treated for shorter or longer than median duration, respectively) and sunflower oil (P=0.0109 and 0.0363 for patients treated for shorter or longer than median duration, respectively) groups (Chi-squared test). Across all patients plaques with a high infiltration of macrophages (i.e. an anti-CD68 staining intensity of 2) contained significantly less EPA and DHA than plaques with a moderate infiltration (i.e. an anti-CD68 staining intensity of 1) (Table 6).

There were no significant differences in the distribution of anti-CD68 staining scores or in the mean ranks of staining intensity between the control and sunflower oil groups.

The T-lymphocyte and macrophage staining observations are summarized in Table 7.

TABLE 5

Carotid plaque morphology in different oil treatment groups

|  |  | Control | Sunflower oil | Fish oil |
|---|---|---|---|---|
| AHA classification[†] | Type III (%) | 1.8 | 0 | 0 |
|  | Type IV (%) | 59.6 | 60.7 | 71.7 |
|  | Type V (%) | 29.8 | 32.2 | 15.1 |
|  | Type VI (%) | 8.8 | 7.1 | 13.2 |
| Modified AHA classification[‡] | Pathological intimal thickening (%) | 7.0 | 7.4 | 7.5 |
|  | Fibrous cap atheroma (%) | 56.1 | 53.7 | 66.0 |
|  | Thin fibrous cap atheroma (%) | 22.8 | 29.6 | 15.1 |
|  | Erosion (%) | 0 | 1.9 | 1.9 |
|  | Plaque rupture (%) | 3.5 | 5.6 | 3.8 |
|  | Calcified nodule and fibrocalcific plaque (%) | 10.5 | 1.9 | 5.7 |

[†]distribution of lesion types significantly different between fish oil and control (P = 0.0234) and fish oil and sunflower oil (P = 0.0107) groups (Chi-squared test).
[‡]distribution of lesion types significantly different between fish oil and control (P = 0.0344) and fish oil and sunflower oil (P = 0.0313) groups (Chi-squared test).

TABLE 7

T lymphocyte and macrophage staining in carotid plaques from patients in different oil treatment groups

|  |  | Control | Sunflower oil | Fish oil |
|---|---|---|---|---|
| Macrophages[‡] | Staining intensity 0 (%) | 2.6 | 0 | 0 |
|  | Staining intensity 1 (%) | 13.2 | 19.4 | 38.1 |
|  | Staining intensity 2 (%) | 84.2 | 80.6 | 61.9 |
|  | Mean rank[†] | 63.5[a] | 61.8[a] | 51.1[b] |

TABLE 6

N-3 polyunsaturated fatty acid content of carotid plaque lipids according to AHA classification and macrophage (anti-CD68) staining intensity

| | Fatty acid (g/100 g total fatty acids) | | | | | |
|---|---|---|---|---|---|---|
| | EPA | | | DHA | | |
| | CE | PL | TAG | CE | PL | TAG |
| AHA Type IV | 1.26 ± 0.08[a] | 0.78 ± 0.06[a] | 0.30 ± 0.03[a] | 1.75 ± 0.08[a] | 3.32 ± 0.13 | 1.01 ± 0.07 |
| AHA Type V | 1.14 ± 0.08 | 0.66 ± 0.08 | 0.28 ± 0.04 | 1.63 ± 0.11 | 3.28 ± 0.19 | 1.03 ± 0.10 |
| AHA Type VI | 1.04 ± 0.16[b] | 0.62 ± 0.17[b] | 0.22 ± 0.07[b] | 1.47 ± 0.21[b] | 2.75 ± 0.23 | 0.97 ± 0.15 |
| Anti-CD68 staining intensity 1 | 1.33 ± 0.09 | 0.67 ± 0.11 | 0.28 ± 0.03 | 1.81 ± 0.09 | 3.18 ± 0.13 | 1.15 ± 0.08 |
| Anti-CD68 staining intensity 2 | 1.19 ± 0.13* | 0.65 ± 0.05 | 0.22 ± 0.05* | 1.63 ± 0.17* | 3.02 ± 0.29 | 0.98 ± 0.15 |

Values for AHA classification indicated by different superscript letters are significantly different from one another (one-factor ANOVA).
*indicates anti-CD68 staining intensity 2 is different from staining intensity 1 (unpaired Student's t-test).

TABLE 7-continued

T lymphocyte and macrophage staining in carotid plaques
from patients in different oil treatment groups

|  |  | Control | Sunflower oil | Fish oil |
|---|---|---|---|---|
| T lymphocytes | Staining intensity 0 (%) | 4.8 | 5.0 | 0 |
|  | Staining intensity 1 (%) | 19.0 | 30.0 | 26.1 |
|  | Staining intensity 2 (%) | 76.2 | 65.0 | 73.9 |
|  | Mean rank | 33.7 | 30.2 | 33.4 |

‡distribution of staining scores significantly different between fish oil and control ($P < 0.0001$) and fish oil and sunflower oil ($P = 0.0016$) groups (Chi-squared test).
†Values across a row indicated by different superscript letters are significantly different from one another ($P = 0.0246$; Jonckheere-Terpstra test).

DISCUSSION

Supplementation of the diet of patients in this study with sunflower oil, providing 3.6 g linoleic acid/day, had only a very limited influence on the outcomes measured. This is probably because these patients were already consuming a significant quantity of linoleic acid in their habitual diet; this intake is in accordance with that reported for adults in the UK. Our observations showed that increasing linoleic acid intake by up to 40% in subjects with advanced carotid atherosclerosis and consuming typical amounts of this fatty acid did not lead to increased linoleic acid incorporation into carotid plaques and did not lead to altered plaque stability, at least over the time period studied.

Supplementation of the diet with fish oil significantly lowered plasma TAG concentration. The degree of TAG lowering was consistent with that seen in other studies of fish oil supplementation, and was related to the duration of fish oil supplementation.

Long chain n-3 PUFA such as EPA and DHA are usually consumed in small quantities, and are therefore found in relatively low proportions in plasma and tissue lipids. However, increased consumption of these fatty acids is marked by an increase in their proportion in various blood and tissue lipid pools, as observed in the present work for LDL lipid fractions. A key observation from the present study is that when long chain n-3 PUFA are consumed at a modest dose they are readily incorporated into atherosclerotic plaque lipids. The incorporation of EPA into plaque lipids, especially PL, was linear with respect to time. The only previous study to examine the effect of fish oil supplementation on the fatty acid composition of atherosclerotic plaques of which we are aware was that of Rapp et al. supra which showed substantial incorporation of EPA and DHA into plaque lipids following consumption of a very high dose of fish oil. However, Rapp et al. did not investigate the effect of EPA/DHA intake of plaque morphology. The present invention has demonstrated that administration of n-3 PUFA at levels that approximate those that have been used in landmark secondary prevention studies (see, e.g. EP-A-1,152,755) are incorporated into plaque lipid pools. Furthermore, even at the modest dosage levels we have used, the incorporation of n-3 PUFA occurs within a relatively short time frame. This suggests that atherosclerotic plaques are fairly dynamic, with some degree of lipid turnover, even at an advanced stage of atherosclerosis.

Immunohistochemical staining and measures of plaque morphology revealed a significant-impact of n-3 PUFA. There were more plaques with a well-formed fibrous cap, rather than a thin inflamed cap, in the fish oil group than in either of the other groups. Furthermore, plaques from patients treated with fish oil were less heavily infiltrated with macrophages. The changes in plaque morphology observed as a result of fish oil supplementation in the present study therefore indicate a more stable plaque, which is less vulnerable to rupture. These differences (i.e. less heavy infiltration with macrophages and more plaques with a well-formed fibrous cap) were related to a higher content of EPA and DHA in the plaque lipids, indicating that it is these n-3 PUFA which determine plaque stability.

Preparation of Medicaments and Mode of Administration

In the present invention the active ingredient of the medicament is EPA, DHA or a mixture of EPA and DHA. These n-3 PUFA fatty acids may be present as the naturally occurring triglyceride form, or they may be in the form of pharmaceutically acceptable salts or derivatives, especially their ethyl esters or other alkyl ester.

Suitably, the active ingredient is derived from fish oil although other sources of EPA and DHA may become commercially available in future years. Methods for manufacturing pharmaceutical grade fish oil from raw fish-oil, and for varying the concentration of the EPA and/or DHA contents in the product, are well known to those skilled in the art. It is preferred from the viewpoints of obtaining a faster uptake of the n-3 PUFA and of ensuring patient compliance that the concentration of EPA and/or DHA in the fish oil should be high, so that an adequate dose can be given by means, for example, of one or two capsules each day. Preferably there is used as the active ingredient a composition containing from 20% to 100% by weight of a mixture of EPA and DHA, more preferably a composition containing more than 70% by weight of the mixture of EPA and DHA, most preferably a composition containing from 70% to 90% by weight of the EPA/DHA mixture. Whilst it is not believed that the ratio of EPA to DHA in the mixture is particularly critical it is usually preferred that the relative amounts of EPA: DHA should be for 1:2 to 2:1, more preferably about 3:2.

Although it is preferred that the active ingredient of the medicament should contain a mixture of EPA and DHA it is written in the scope of this invention to use either of these n-3 PUFA acids by itself. Methods for preparing essentially pure EPA or DHA are known and are described in the literature.

The medicament of the present invention is for oral administration. Suitably the oral form is a hard or soft shell capsule, although other oral forms eg powder obtained through microencapsulation can be used if desired.

The medicaments may comprise, in addition to the EPA and DHA active ingredients as defined, one or more pharmaceutically acceptable carrier as well known in the art. The compositions can also include fillers, stabilizers, extenders, binders, humidifiers, surfactants, lubricants and the like, as shown in the art of formulating pharmaceutical compositions.

In addition antioxidants, for example hydroxytoluene, butyrate, quinone, tocopherol, ascorbic acid etc., preservatives, colouring agents, perfumes, flavourings and other pharmaceutical agents may be used. An antioxidant is a particularly preferred optional component of the medicaments.

Example of Oral Medicament Preparation

Soft Gelatine Capsules Containing 1 g/per Capsule Composition:

| | |
|---|---|
| EPA ethyl ester | 525 mg/capsule |
| DHA ethyl ester | 315 mg/capsule |
| d-alpha Tocopherol | 4 IU/capsule |
| Gelatine | 246 mg/capsule |
| Glycerol | 118 mg/capsule |

The active ingredients and the excipients are weighted and homogenized on a high speed stirrer. The mixture is then colloid milled and deareated in a stainless steel vessel ready for encapsulation. The mixture is filled in soft gelatine capsules of size 20 oblong, (average weight 1.4 g) using a standard encapsulation machine.

The medicament of the present invention may be administered to patients with symptoms of atherosclerosis of arteries supplying the brain at any suitable dose, the n-3 PUFA being essentially non-toxic even at quite high dosage levels. In the trial described above the dosage regimen was such as to provide about 1.4 g of EPA and DHA total per day, and this was shown to be effective to increase plaque stability. Generally, the dosage will range from 0.5 to 5.0 g of EPA and/or DHA daily, with the preferred dosage being from 1.0 to 3.0 g/daily.

The medicament of the invention is suitably administered to patients with symptoms of atherosclerosis of arteries supplying the brain, for instance a stroke or a transient ischaemic attack, in order to reduce the risk of a further, possibly fatal, attack. To this end the medicament may also be utilized in conjunction with other therapeutic agents, for example aspirin and warfarin, known to reduce the risk of secondary neurological events in such patients.

The invention claimed is:

1. A method for increasing the stability of carotid plaques in a patient having had a symptom of at least one of transient ischemic attack and amaurosis fugax comprising administering to the patient having had a symptom of at least one of transient ischemic attack and amaurosis fugax a composition comprising eicosapentaenoic acid (EPA), docosahexaenoic acid (DHA), or a mixture of EPA and DHA, in a form chosen from pharmaceutically acceptable salts thereof, ethyl esters thereof, triglycerides thereof, and other alkyl esters thereof, wherein the composition increases the concentration of the EPA, DHA, or mixture thereof, in the patient's carotid plaque lipids, thereby increasing the stability of the carotid plaques,
   wherein EPA, DHA, or mixtures thereof are the sole active agent,
   wherein the composition is administered at a dosage ranging from 0.5 g/day to 5.0 g/day.

2. The method of claim 1, wherein the composition comprises a mixture of EPA and DHA.

3. The method of claim 2, wherein the ratio of EPA to DHA in the mixture is from 1:2 to 2:1.

4. The method of claim 3, wherein the ratio is approximately 3:2.

5. The method of claim 2, wherein EPA and DHA are present as ethyl esters.

6. The method of claim 1, wherein EPA, DHA, or a mixture thereof is present in the composition in an amount between 20% to 100% by weight of the composition.

7. The method of claim 6, wherein EPA, DHA, or a mixture thereof is present in the composition in an amount greater than 70% by weight of the composition.

8. The method of claim 7, wherein EPA, DHA, or a mixture thereof is present in the composition in an amount between 70% and 90% by weight of the composition.

9. The method of claim 1, wherein the composition is administered at a dosage from 1.0 g/day to 3.0 g/day.

10. The method of claim 1, wherein the composition is in capsule form.

* * * * *